United States Patent [19]

Takekoshi et al.

[11] 4,349,479

[45] Sep. 14, 1982

[54] METHOD OF SALVAGING AROMATIC BISIMIDE VALUES

[75] Inventors: Tohru Takekoshi, Scotia; Jimmy L. Webb, Ballston Lake, both of N.Y.

[73] Assignee: General Electric Company, Schenectady, N.Y.

[21] Appl. No.: 124,914

[22] Filed: Feb. 26, 1980

[51] Int. Cl.$^3$ .................. C07D 403/12; C07B 29/00; C07D 403/06; C07D 487/04
[52] U.S. Cl. ........................... 260/326 N; 260/326 S; 260/326 C
[58] Field of Search ............ 260/326 C, 326 S, 326 N

[56] References Cited

U.S. PATENT DOCUMENTS

| | | | |
|---|---|---|---|
| 3,529,017 | 9/1970 | Izard | 544/229 |
| 3,847,870 | 11/1974 | Takekoshi | 260/47 CP |
| 3,850,885 | 11/1974 | Takekoshi | 260/47 CZ |
| 4,128,574 | 12/1978 | Markezich | 260/326 A |

*Primary Examiner*—Mark L. Berch
*Attorney, Agent, or Firm*—William A. Teoli; James C. Davis, Jr.

[57] ABSTRACT

A method of recovering aromatic bis(N-alkylimide)s from aqueous aromatic polyimide-alkyl amine aminolysis mixtures is provided by heating the aromatic polyimide in the presence of water and alkyl amine. The resulting aromatic bis(N-alkylimide)s can be converted to aromatic dianhydride by aromatic bisimide-organic amine exchange reactions.

7 Claims, No Drawings

METHOD OF SALVAGING AROMATIC BISIMIDE VALUES

BACKGROUND OF THE INVENTION

Prior to the present invention, as shown by U.S. Pat. No. 3,847,870, Takekoshi and U.S. Pat. No. 3,850,885, Takekoshi et al, assigned to the same assignee as the present invention, an imide-amine exchange reaction is taught for making polyetherimides catalyzed by Group (II-V) basic metals and compounds and metals and compounds derived therefrom. Displacement of organic monomeric amine from the bisimide can be effected under melt conditions with organic diamine.

Although amine interchange is a valuable route to the manufacture of polyimides, as shown by Takekoshi et al U.S. Pat. No. 3,850,885, in particular situations it is often desirable to salvage bisimide values from polyimide samples in the form of chips or reground granules to use such salvage values in the further production of polyimides. It would be desirable, for example, to be able to salvage bisimide values from scrap polyimide in the form of N-alkyl substituted bisimide which can be readily converted to the corresponding organic dianhydride as shown, for example, by Markezich et al U.S. Pat. No. 4,128,574, assigned to the same assignee as the present invention, based on an imide-anhydride exchange reaction.

STATEMENT OF THE INVENTION

The present invention is based on the discovery that aromatic polyimide consisting essentially of chemically combined units of the formula,

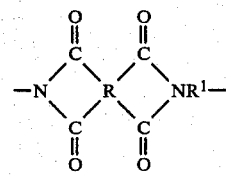

where R is a tetravalent $C_{(6-30)}$ aromatic organic radical, and $R^1$ is a divalent $C_{(1-20)}$ organic radical, can be converted to bis-(N-alkylimide) by heating such polyimide in the presence of $C_{(1-12)}$ alkyl amine and water. A simple aminolysis reaction has been found to occur in aqueous media based on an imide-amine interchange reaction allowing for the recovery of aromatic diamine and aromatic bis(N-alkylimide) from the reaction mixture.

There is provided by the present invention a method which comprises, (1) heating at a temperature in the range of from 100° C. to 300° C., a mixture comprising, aromatic polyimide consisting essentially of chemically combined units of formula (1), a $C_{(1-12)}$ alkyl amine and water, where sufficient alkyl amine is utilized in the mixture to substantially maintain stoichiometric equivalents between the alkyl amine and the polyimide units of formula (1) and (2) recovering aromatic bis(N-alkylimide) from the mixture of (1).

Radicals included within R of formula (1) are more particularly:

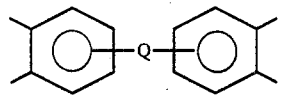

where Q is selected from —O—, —S—,

and —O—$R^2$—O— and $R^2$ is a divalent organic radical selected from

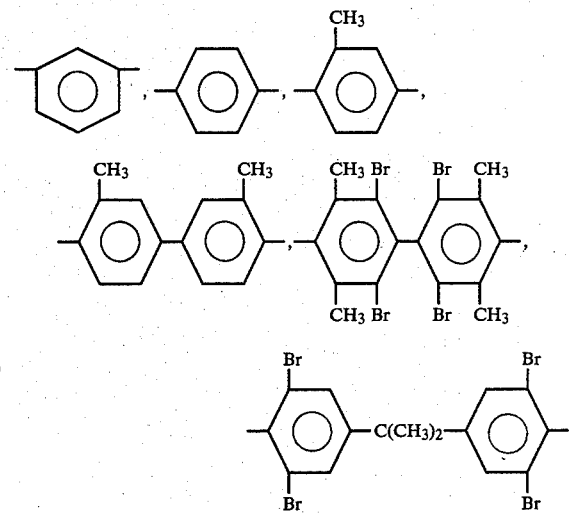

and organic radicals of the general formula,

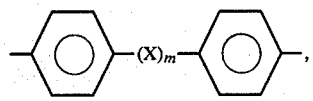

where X is a member selected from the class consisting of divalent radicals of the formulas —$C_yH_{2y}$—,

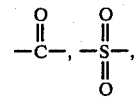

—O— and —S—, where m is 0, or 1 and y is a whole number from 1 to 5.

Radicals included by $R^1$ of formula (1) are divalent organic radicals selected from the class consisting of (a) aromatic hydrocarbon radicals having from 6-20 carbon atoms and halogenated derivatives thereof, (b) alkylene radicals, $C_{(2-8)}$ alkylene terminated polydiorganosiloxane cyclo-alkylene radicals having from 2-20 carbon atoms, and (c) divalent radicals included by the formula,

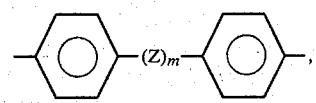

where Z is a member selected from the class consisting of —O—

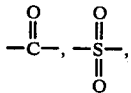

—S—, —$C_xH_{2x}$— and x is a whole number from 1 to 5 inclusive, and m is 0 or 1.

Polyimides which can be used in the practice of the present invention and which consist essentially of imide units within formula (1) are, for example, polyetherimides as described by Heath et al, U.S. Pat. No. 3,847,867, assigned to the same assignee as the present invention and Upjohn Polyimide 2080. Some of the polyimides which can be used in the practice of the invention to obtain aromatic bis(N-alkylimide) values are polymers or oligomers consisting essentially of the following chemically combined units:

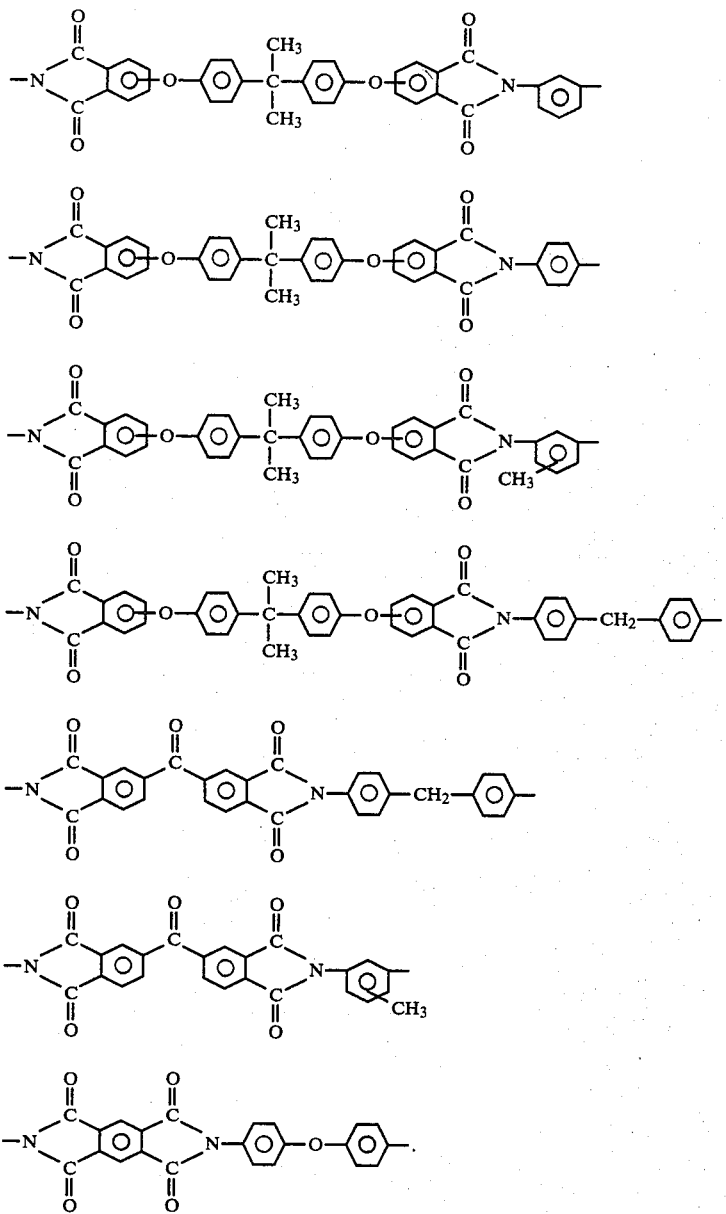

The aromatic bis(N-alkylimide) which can be obtained in the practice of the invention have the formula,

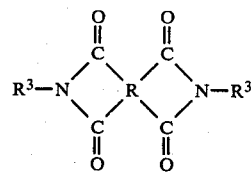

where R is as previously defined and $R^3$ is a $C_{(1-8)}$ alkyl radical, such as methyl, ethyl, propyl, butyl, pentyl, hexyl, heptyl, and octyl.

Compounds included by the aromatic bis(N-alkylimide)s of formula (2) are, for example,

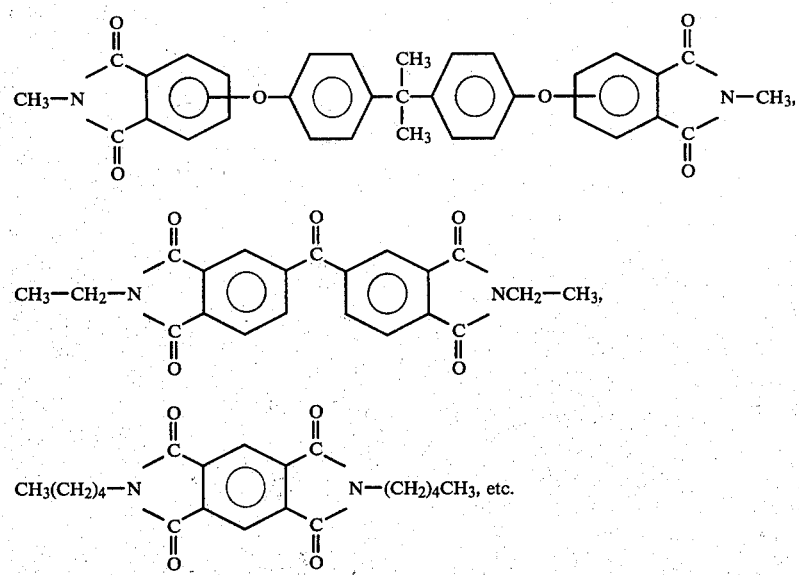

In the practice of the invention a mixture of the polyimide and N-alkyl amine and water is heated at a temperature of at least 100° C. and to as high as 300° C. for a period of from 0.5 to 10 hours along with agitation if desired. The mixture is preferably heated under sealed conditions, such as in an autoclave, particularly if a volatile N-alkylamine is used. N-alkylamines which can be employed are, for example, methylamine, ethylamine, propylamine, butylamine, pentylamine, hexylamine, heptylamine, octylamine, etc. The polyimide is preferably pulverized to facilitate the amine water interaction. The resulting aromatic bis(N-alkylimide) can be isolated by filtration and thereafter purified by standard procedures, such as recrystallization, if desired.

Although the amount of water in the original mixture is not critical it is preferred to utilize about 0.1 to 20 parts of water per part of polyimide during the reaction.

As previously indicated, a stoichiometric equivalence or more of the N-alkylamine and the polyimide units should be maintained during the reaction to achieve an effective aminolysis of polyimide.

In order that those skilled in the art will be better able to practice the invention, the following examples are given by way of illustration and not by way of limitation. All parts are by weight.

EXAMPLE 1

A mixture of 50 parts of polyimide, 15.27 parts of a 40% aqueous solution of methylamine and 440 parts of water were charged in an autoclave. The polyimide consisted essentially of chemically combined units of the formula,

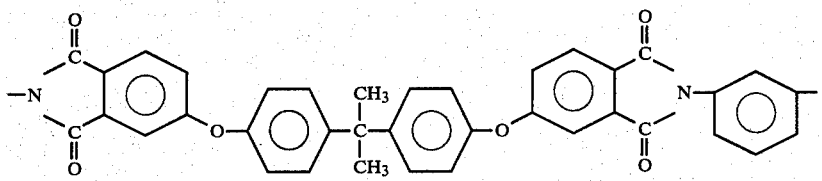

The mixture was stirred and heated at 400° F. and a pressure of 280 psi was maintained for 1.5 hours. The aqueous phase was removed and the residue was dissolved in about 200 parts of toluene. The mixture of the toluene solution and 100 parts of water was heated at 150° C. in an autoclave and cooled. The toluene phase was separated, filtered and evaporated to dryness. There was obtained 45.5 parts of product representing a yield of 98.7%. Based on method of preparation and its melting point, the product was a bisimide of the formula,

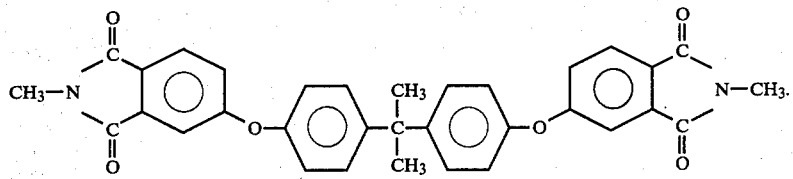

The aqueous phase was also filtered and evaporated to dryness. There was obtained 13.7 parts of crude m-phenylenediamine which represented a yield of about 81%.

The above described aromatic bis(N-alkylimide) was heated in the presence of phthalic anhydride and water in accordance with the procedure of Webb U.S. Pat. No. 4,116,980. There is obtained a quantitative yield of the corresponding aromatic bis(ether anhydride) of the formula,

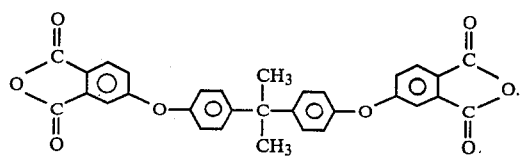

EXAMPLE 2

A mixture of 40 parts of Upjohn Polyimide 2080, 13 parts of a 70% aqueous ethylamine solution, 100 parts of water was heated and stirred at 180° C. for 3 hours under sealed conditions. The mixture was cooled and solid precipitate of a product was recovered by filtration. There was obtained 29.5 parts of product which represented a yield of 91.3%. Based on method of preparation, the product was the aromatic bis(alkylimide) of the formula,

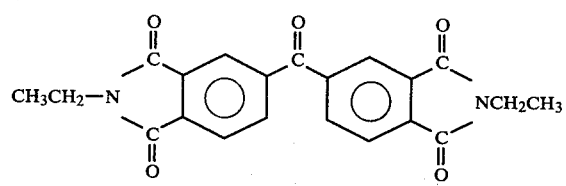

Although the above examples are directed to only a few of the very many variables within the scope of the present invention, it should be understood that the present invention is directed to a much broader method based on the use of polyimide consisting essentially of polyimide imide units of formula (1) and mixtures thereof and $C_{(1-12)}$ alkyl amine and mixtures thereof.

What we claim as new and desire to secure by Letters Patent of the United States:

1. A method which comprises:
   (1) heating at a temperature in the range of from 100° C. to 300° C., a mixture comprising aromatic polyimide consisting essentially of chemically combined units of the formula,

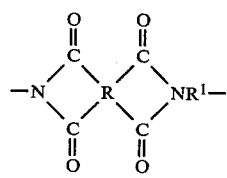

a $C_{(1-12)}$ alkyl amine and water, where sufficient alkyl amine as utilized in the mixture to substantially maintain stoichiometric equivalence between the alkyl amine and units of polyimide and
   (2) recovering aromatic bis(N-alkylimide) from the mixture of (1), where R is a $C_{(6-30)}$ tetravalent aromatic organic radical selected from

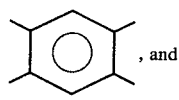, and

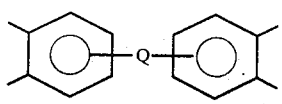, where Q is selected from —O—, —S—,

and —O—R²—O— and R² is a divalent organic radical selected from

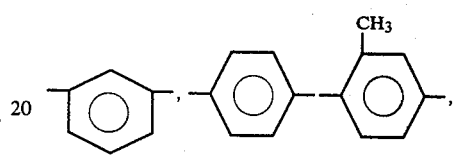

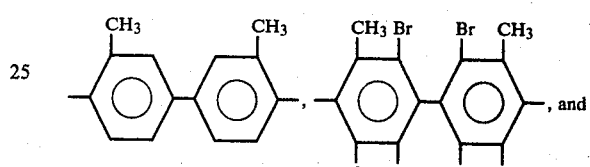, and

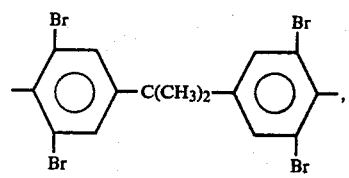

and organic radicals of the formula,

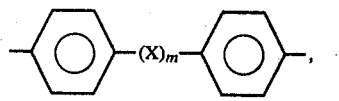, where X is a member selected from the class consisting of divalent radicals of the formulas:

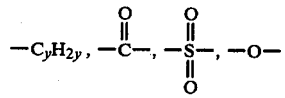

and —S—, where m is 0 or 1 and y is a whole number from 1 to 5, and $R^1$ is a $C_{(2-20)}$ divalent organic radical selected from the class consisting of (a) aromatic hydrocarbon radicals having from 6-20 carbon atoms and halogenated derivatives thereof, (b) alkylene radicals having from 2-20 carbon atom, and (c) divalent radicals of the formula,

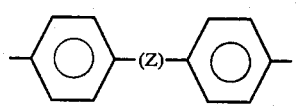

where Z is a member selected from the class consisting of —O—,

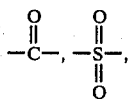

—S—, —$C_xH_{2x}$— and x is a whole number from 1 to 5 inclusive.

2. A method in accordance with claim 1, where the polyetherimide consists essentially of chemically combined units of the formula,

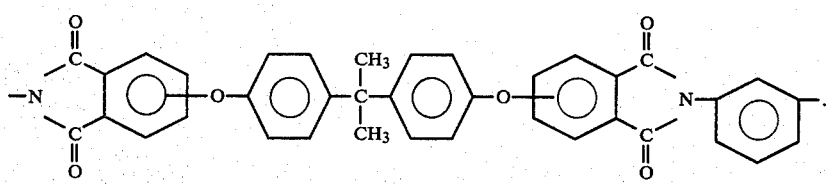

3. A method in accordance with claim 1, where the polyetherimide consists essentially of chemically combined units of the formula,

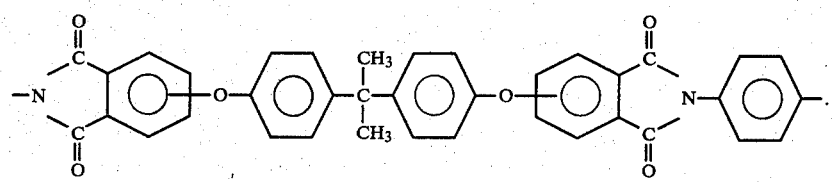

4. A method in accordance with claim 1, where $R^1$ is

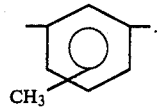

5. A method in accordance with claim 1, where $R^1$ is

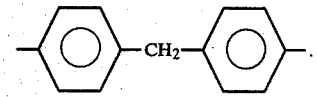

6. A method in accordance with claim 1, where the N-alkyl amine is methylamine.

7. A method in accordance with claim 1, where the N-alkylamine is ethylamine.

* * * * *